(12) United States Patent
Crawford

(10) Patent No.: US 6,949,382 B2
(45) Date of Patent: Sep. 27, 2005

(54) CELL CULTURE MEDIA CONTAINING N-ACETYL-L-CYSTEINE AND USES THEREOF

(75) Inventor: J. Fred Crawford, Houston, TX (US)

(73) Assignee: Research Development Foundation, Carson City, NV (US)

( * ) Notice: Subject to any disclaimer, the term of this patent is extended or adjusted under 35 U.S.C. 154(b) by 0 days.

(21) Appl. No.: 10/696,334

(22) Filed: Oct. 29, 2003

(65) Prior Publication Data

US 2004/0087023 A1 May 6, 2004

Related U.S. Application Data

(62) Division of application No. 10/017,625, filed on Dec. 13, 2001, now Pat. No. 6,709,835, which is a division of application No. 08/922,279, filed on Sep. 3, 1997, now abandoned.
(60) Provisional application No. 60/025,373, filed on Sep. 3, 1996.

(51) Int. Cl.[7] .................................................. C12N 5/00
(52) U.S. Cl. ...................................... 435/404; 435/405
(58) Field of Search ........................... 435/404, 14, 29, 435/244, 375, 405

(56) References Cited

U.S. PATENT DOCUMENTS

| | | | |
|---|---|---|---|
| 4,499,064 A | 2/1985 | Shive | 435/14 |
| 4,927,762 A | 5/1990 | Darfler | 435/387 |
| 5,171,885 A | 12/1992 | Griffith | 562/556 |
| 5,290,571 A | 3/1994 | Bounous et al. | 424/535 |
| 5,326,699 A | 7/1994 | Torishima et al. | 435/384 |
| 5,405,772 A | 4/1995 | Ponting | 435/378 |
| 5,607,974 A | 3/1997 | Droge et al. | 514/562 |
| 5,985,665 A * | 11/1999 | Crawford et al. | 435/404 |
| 6,262,019 B1 | 7/2001 | Keller et al. | 514/2 |
| 6,514,955 B1 | 2/2003 | Van Dyke | 514/171 |
| 6,709,835 B2 * | 3/2004 | Crawford | 435/25 |
| 2002/0136763 A1 | 9/2002 | Demopoulos et al. | 424/451 |

OTHER PUBLICATIONS

Fidelus et al., "Modulation of intracellular glutathione concentrations alters lymphocyte activation and proliferation," *Exp. Cell Res.*, 170:269–275, 1987.

Hamilos et al., "Lymphocyte proliferation in glutathione–depleted lymphocytes: direct relationship between glutathione availability and the proliferative response," *Immunopharmacology*, 18:223–225, 1989.

Messina et al., "Effects of 2–mercaptoethanol and buthionine sulfoximine on cystine metabolism by and proliferation of mitogen–stimulated human and mouse lymphocytes," *Int. J. Immunopharmacology*, 14:1221–1234, 1992.

* cited by examiner

*Primary Examiner*—Ralph Gitomer
(74) *Attorney, Agent, or Firm*—Fulbright & Jaworski

(57) ABSTRACT

The present invention provides cell culture media and methods useful for determining levels of intracellular function of glutathione or cysteine and for providing biochemical analysis of antioxidant function in human lymphocytes.

16 Claims, No Drawings

CELL CULTURE MEDIA CONTAINING N-ACETYL-L-CYSTEINE AND USES THEREOF

CROSS-REFERENCE TO RELATED APPLICATIONS

This is a divisional of U.S. Ser. No. 10/017,625, filed Dec. 13, 2001 now U.S. Pat. No. 6,709,835, which is a divisional of U.S. Ser. No. 08/922,279, filed Sep. 3, 1997, now abandoned which claims priorty to provisional application 60/025,373 filed Sep. 3, 1996.

BACKGROUND OF THE INVENTION

1. Field of the Invention

The present invention relates generally to the fields of nutrition and biochemistry and cellular glutathione metabolism. More specifically, the present invention relates to measurement of levels of intracellular function of cysteine and glutathione so as to provide one measurement an individual's capability of preventing degenerative disease and dealing with oxidative stress.

2. Description of the Related Art

It is now accepted widely that a number of human health conditions, including aging, arthritis, cancer, atherosclerosis, myocardial infarction, stroke, viral infection, pulmonary conditions, bowel disease and neurodegenerative disease, can develop or be worsened by the presence of reactive oxygen molecules, commonly referred to as free radicals. These hostile molecules are normal by-products of physiological processes and are produced by metabolism of oxygen; e.g., via cellular respiration or immune system function (killing of foreign materials), and by numerous enzymatic reactions essential for metabolism. In addition, free radicals are found commonly in the environment. Environmental sources of free radicals include smoke, ionizing radiation, air pollution, chemicals (carcinogens, many petrochemicals, biocides, dyes, solvents, cytostatic drugs, etc.), toxic heavy metals and oxidized or rancid fats. Some of the most common free radicals are super oxide, hydroxyl radical, singlet oxygen, and peroxides, including hydrogen peroxides. Certain valences of iron and copper can catalyze formation of free radicals, which, although short-lived, promote a chain reaction of radical formation, followed by a wake of altered, damaged biological molecules.

Free radicals are toxic to living organisms, causing structural damage to biological molecules. Molecular damage may result in alteration of genetic codes, disruption of cell membrane integrity, neurological disorders, endocrine imbalances, increased allergies, vascular endothelial destruction and joint degradation and inflammation.

Protection from the deleterious effects of free radicals is found in a diverse range of molecules termed antioxidants. Free radicals and their chain by-products can be neutralized and converted to less harmful products by antioxidants. Antioxidants may be enzymes (such as superoxide dismutase, catalase, glutathione peroxidase), essential nutrients (such as beta carotene, vitamins C and E, selenium) or a wide variety of endogenous compounds (such as glutathione) or dietary compounds (such as the bioflavanoids). Thus, the human body has several, natural quenchers of free radicals.

Research in humans has indicated that deficient intakes of nutrient antioxidants are associated with higher risks of cancer, cardiovascular disease, arthritis, cataracts, etc. Also, a higher intake of nutrient antioxidants is associated with lower incidence of chronic degenerative diseases. Encouraging studies indicate that intervention with antioxidant nutrient supplements may have therapeutic benefit in humans.

Laboratory analysis of antioxidant status has not become routine for a variety of reasons. Free radicals are extremely fleeting and generally are not amenable to direct measurement. By-products of free radical damage can be measured, such as malondialdehyde (MDA), thiobarbituric acid-reactive substances (TBARS) or lipid peroxides in serum or urine; however, these tests may be indicators of oxidative stress but reflect only damage to certain types of biomolecules (mostly polyunsaturated lipids and nucleic acids). Yet methods of measurement of antioxidant nutrient levels in serum or cells and activities of antioxidant enzymes in cells could identify deficient levels of specific components.

Glutathione is a preeminent cellular antioxidant substance which is abundant in cytoplasm, nuclei and in mitochondria. In addition to glutathione's powerful antioxidant function, it serves also as a powerful anti-toxin, allowing the body to eliminate numerous xenobiotic and carcinogenic compounds. Further, glutathione is essential for cell-mediated immune functions and it is critical to the maintenance of the integrity of red blood cells. Moreover, it is recognized generally that deficiencies in the glutathione system lead to significant cellular aging, and, ultimately, cellular morbidity.

The concentration of cellular glutathione has a significant effect on antioxidant function; and nutrient limitation, exercise and oxidative stress have significant effects on cellular glutathione concentrations. Under oxidative conditions, glutathione function can be depleted considerably through conjugation to xenobiotics, and by secretion of glutathione conjugates and glutathione disulfide from the affected cells. A considerable amount of glutathione may become protein bound during severe oxidative stress. Fortunately, however, compounds such as N-acetyl-cysteine are available to increase intracellular glutathione function.

Glutathione is synthesized in a series of biochemical reactions utilizing ATP, magnesium and the three amino acids glycine, glutamate and cysteine. In general, the rate of synthesis of gamma-glutamylcysteine determines the rate of synthesis of glutathione, and the sulfhydral group of cysteine provides glutathione with its biological potency. Thus, measurement of cysteine availability is essential in determining the functional availability of glutathione and in the assessment of antioxidant function.

Assessment of cysteine and glutathione also is helpful in assessing selenium deficiency. When glutathione functions as an antioxidant, it reacts with hydrogen peroxide to form glutathione disulfide in a reaction catalyzed by glutathione peroxidase. Glutathione peroxidase requires selenium as a functional cofactor. Thus, adequate cysteine function, combined with deficient or average SPECTROX™ results, is indicative of an intracellular selenium deficiency and calls for further testing.

The prior art is deficient in the lack of simple cost-effective means of assessing biochemically the levels of intracellular function of cysteine and glutathione in a human, and thus an individual's capability of dealing with oxidative stress. The present invention fulfills this long-standing need and desire in the art.

SUMMARY OF THE INVENTION

One object of the present invention is to provide a cell cuture medium useful for determining a levels of intracellular function of glutathione in lymphocytes and for performing biochemical analysis of antioxidant function, said medium comprising a buffered, serum-free solution containing the following ingredients: a carbohydrate selected from the group consisting of glucose or a compound biologically capable of producing glucose in the cells; a biologically usable form of pantothenic acid, choline or a biologically utilizable form of a substance capable of producing choline in the cells; inorganic ions comprising chloride, phosphate, calcium, magnesium, potassium, sodium, and iron in a biologically utilizable form; L-Buthionine-[S.R.]-Sulfoximine; deionized water; and a mitogen in an amount effective to stimulate the lymphocytes being assayed; said buffered, serum-free solution having a pH from about 6.8 to 7.6; and wherein said cell culture medium is characterized by being effective to determine an levels of intracellular function of glutathione in lymphocytes, nutritional deficiencies, inadequacies, and imbalances and to analyze biochemically antioxidant function of the lymphocytes.

One embodiment of the present invention includes supplementing the cell medium of the present invention with a nutrient supplement selected from the group consisting of biological utilizable forms of amino acids and vitamins, the nutrient being tested for being omitted from or being present in limiting or inhibitory amounts in the nutrient supplement.

Another object of the present invention is to provide a method of determining a levels of intracellular function of glutathione and analyzing biochemically cellular antioxidant function in an individual, comprising the steps of: inoculating the cell culture medium of the present invention with lymphocytes from an individual to be tested; incubating the inoculated cell culture medium; and comparing the response of the lymphocytes with an average response of lymphocytes from a control group of individuals.

A further object of the present invention is to provide a cell cuture medium useful for determining the level of intracellular function of cysteine and performing biochemical analysis of antioxidant function in human lymphocytes, said medium comprising a buffered, serum-free solution containing the following ingredients: a carbohydrate selected from the group consisting of glucose or a compound biologically capable of producing glucose in the cells; a biologically utilizable form of pantothenic acid, choline or a biological usable form of a substance capable of producing choline in the cells; inorganic ions comprising chloride, phosphate, calcium, magnesium, potassium, sodium, and iron in a biologically utilizable form; cumene hydroperoxide; deionized water; N-Acetyl-L-Cysteine; and a mitogen in an amount effective to stimulate the lymphocytes being assayed; said buffered, serum-free solution having a pH from about 6.8 to 7.6, said cell culture medium characterized by being effective to determine nutritional deficiencies, inadequacies, and imbalances and to analyze biochemically antioxidant function of the lymphocytes.

One embodiment of the present invention includes supplementing the cell medium of the present invention with a nutrient supplement selected from the group consisting of biologically utilizable forms of amino acids and vitamins, the nutrient being tested for being omitted from or being present in limiting or inhibitory amounts in the nutrient supplement.

An additional object of the present invention is to provide a method of determining a level of intracellular function of cysteine and analyzing biochemically cellular antioxidant function in an individual comprising the steps of: inoculating the cell culture medium of the present invention with lymphocytes from an individual; incubating the inoculated cell culture medium; and comparing the response of the lymphocytes with an average response of lymphocytes from a control group of individuals.

Other and further aspects, features, and advantages of the present invention will be apparent from the following description of the presently preferred embodiments of the invention. These embodiments are given for the purpose of disclosure.

DETAILED DESCRIPTION OF THE INVENTION

The present invention is directed to a method useful for the biochemical analysis of levels of intracellular function of cysteine and glutathione in human lymphocytes. Such an analysis reflects the physiological health of an individual's antioxidant systems within the peripheral lymphocytes. The methodology of the present invention allows precise assessment of the intracellular function of cysteine and glutathione in human lymphocytes, so that therapeutic measures can be taken to improve an individual's antioxidant profile.

The present method, utilizing lymphocytes, offers distinct advantages, as lymphocytes: (1) are host to the cell-mediated immune system and are easily stimulated to grow (mitogenesis); (2) reflect time-averaged, long-term nutrient status (the life of a lymphocyte is about six months); (3) possess metabolic pathways common to other cells, and (4) are easily collected by standard venipuncture.

By measuring lymphocyte growth to assess intracellular function of cysteine and glutathione, the method of the present invention reflects the unique profile of each patient, which varies widely. Therapeutic treatment, therefore, can be tailored to the specific biochemical requirements of the individual rather than the "average" patient as determined by so-called norms.

It will be apparent to one skilled in the art that various substitutions and modifications may be made to the invention disclosed herein without departing from the scope and spirit of the invention. The following examples are given for the purpose of illustrating various embodiments of the invention and are not meant to limit the present invention in any fashion.

EXAMPLE 1
Drawing Patient's Blood

Two 10 ml whole blood specimens preserved with acidcitrate-dextrose are required for the method of the present invention. No fasting is required. All that is required are blood drawing supplies. The assay of the present invention may be performed or the patient's blood should be shipped at room temperature to a suitable laboratory. No centrifuging of the blood is required. Comprehensive test results provided a sound, scientifically-based analysis of the patient's glutathione or cysteine profile.

EXAMPLE 2
Sample Processing: Cell Isolation

All procedures are conducted using sterile techniques under a laminar flow hood to insure sample sterility. Each patient's blood samples are assigned an Accession number upon receipt at the laboratory. This accession number is used as the sample number to enable tracking throughout processing, data collection and data analysis steps. Every test tube, centrifuge tube, microtiter plate and data printout involved with processing the patients sample is labeled with this sample (accession) number.

Each patient sample consists of (2) two Acid-Citrate-Dextrose (yellow top) vaccutainer type tubes, each containing 8 ml of whole blood. After being assigned an accession (sample) number, the whole blood was mixed by inverting 6 times. The two tubes of whole blood were combined into a 50 ml disposable centrifuge tube.

A 500 µl aliquot was removed aseptically from each sample and placed in a 12×17 mm tube. This aliquot was used to perform a whole blood cell count on the Coulter Cell Counter, Model T540. The whole blood cell count printout from the Coulter was labeled with the accession number and attached to the Worksheet for that patient.

Two (2) Ficoll gradient tubes were prepared for each sample by the addition of 5.0 ml of Histopaque 1077 (Ficoll/Sodium Diatrizoate, Sigma Chemicals, St. Louis, Mo.) to each 15 ml conical centrifuge tube. Using a 10 ml pipette and an electric pipette aid, 8 ml of whole blood is slowly layered onto each of the Ficoll gradient tubes. The Ficoll gradient tubes were capped and centrifuged at 2160 RPM for 20 minutes.

After centrifugation was complete, the gradient tubes were carefully removed from the centrifuge to avoid disrupting the gradient. The buffy coat (containing the lymphocytes) found at the interface of the middle Ficoll layer was transferred using a 5 ml pipette into a 15 ml disposable conical centrifuge tube. The buffy coat was combined with phosphate buffered saline-0.72% glucose solution (PBS-G) to a final volume of 12 ml. The tube was capped and inverted 6 times to mix the buffy coat and the PBS-G.

The tubes containing buffy coat and PBS-G were centrifuged at 2160 RPM for 5 minutes. After centrifugation, the supernatant was aspirated from the cell pellet and discarded. The cell pellet was resuspended into 12 ml of PBS-G, then inverted 6 times to insure adequate dispersal of the cell pellet. The sample was then centrifuged again as described above.

After the second centrifugation, the supernatant was aspirated and discarded. The cell pellet was resuspended in 6.0 ml of PBS-G. The cell pellet was disrupted and mixed with the PBS-G using a 5 ml pipette attached to an electric pipet aide. After a homogeneous cell suspension has been attained, a 200 µl aliquot of the suspension was transferred into a 12×75 mm tube. This aliquot was used to perform the initial cell suspension (ICS) count with the Coulter Cell Counter Model T540.

The printout from this aliquot was labeled with the sample number and attached to the Worksheet. If the lymphocyte number was between 3.9 and 1.2 thousand cells per cubic millimeter (THSD/mm$^3$) the sample is ready for plate inoculation. The volume of cell suspension to be added is found in TABLES I and IV. If the lymphocyte number was greater than 3.9 THSD/mm$^3$, the sample must be rediluted. If, however, the lymphocyte number was less than 1.2 THSD/mm$^3$, the sample was rejected.

The amount of additional PBS-G that is required for proper redilution was determined using the following calculations:

$C_1, V_1 = C_2 V_2 C$ = Lymphocyte Concentration (THSD/mm$^3$)

V=Volume

Where $C_2$=3.0 THSD/mm$^3$, this was the desired lymphocyte concentration of the final cell suspension. For example, when the initial Cell Suspension Count from 6.0 ml=(LY# of 5.6 THSD/mm$^3$)

$C_1, V_1 = C_2 V_2$ (5.6)(6.0 ml)=(3.0)(X)

X=11.2 ml final volume.

An appropriate volume of PBS-G was added to resuspend cells for a final volume of 11.2 ml. In this example, 5.2 ml would be added to the original 6.0 ml for a final volume 11.2 ml. The required volume of PBS-G was added to the (ICS) to make the Final Cell Suspension (FCS). The LY# count and PBS-G volume were recorded on the SPECTROX™ Test Worksheet.

After redilution, a 200 µl aliquot of the rediluted cell suspension was transferred into a new 12×75 mm tube and a cell count performed as described. The rediluted cell suspension printout (Final Cell Suspension LY#) was attached to the Worksheet and the inoculation volume recorded.

EXAMPLE 3

Assessment of Glutathione Concentration Plate Inoculation

The final cell suspension was placed into a sterile trough and a microtiter plate containing media was placed inside a laminar flow hood. Using a 12-channel manual micropipettor equipped with sterile 0-50 µl barrier tips, the specified amount (according to TABLE I) of final cell suspension was dispensed to each well of the plate.

TABLE I

The following volumes are used for plate inoculation based on the listed final cell suspension Lymphocyte number (LY#).

| Final Cell Suspension LY# | Adjusted Volume For Inoculation |
|---|---|
| 3.9–.37 | 8.0 µl |
| 3.6 | 8.5 µl |
| 2.5–3.5 | 10.0 µl |
| 2.4 | 12.5 µl |
| 2.3 | 13.0 µl |
| 2.2 | 14.0 µl |
| 2.1 | 14.5 µl |
| 2.0 | 15.0 µl |
| 1.9 | 16.0 µl |
| 1.8 | 17.0 µl |
| 1.7 | 18.0 µl |
| 1.6 | 19.0 µl |
| 1.5 | 20.0 µl |
| 1.4 | 21.5 µl |
| 1.3 | 23.0 µl |
| <=1.2 | 25.0 µl |

After addition of the cells to the media, the plates were covered and placed in a CO$_2$ incubator maintained at 37° for 96 hours.

Labeling

All labeling procedures were performed in the Radioisotope Room. The tritiated thymidine (H$^3$-TdR) working solution was removed from the refrigerator and warmed to 37° C. in a water bath. After 96 hours, the microtiter plates were removed from the incubator. The H$^3$-TdR working solution was placed in a sterile trough and a 12-channel manual micropipettor equipped with 0–50 µl sterile barrier tips was used to dispense 10 µl of the H$^3$-TdR working solution into each well of the microtiter plate. The plate was returned to the 37° C. incubator for 24 hours. The date and initials of the technician performing the labeling was recorded on the sample log sheet.

Harvesting

All harvesting procedures were performed in the Radio-isotope Room. A single glass fiber filter mat (Packard Part # 6005416) was labeled with the sample number using a #2 pencil. The vacuum pump was turned on and the drying oven set at 100° C. The distilled water carboy attached to the harvester was filled. The microtiter plates were removed from the incubator 24 hours after the addition of H$^3$-TdR. The date and initials of the technician performing harvesting was recorded on the sample log sheet.

With the Cell Harvester (Packard Model # C9619) in the open position, O-Rings exposed, the glass fiber filter mat was placed onto the harvester with the rough side touching the O-Rings. The cell harvester was closed and the filter mat was wet with distilled water from the rinse tray. The harvester was left on vacuum cycle (VAC). The lid was removed from microtiter plate and the plate was placed under harvester probe tips. The plate was slowly raised onto harvester probes, until the tips of the probe touched the bottom of the plate. With the media aspirated, the bottoms of the wells were scrubbed with the probe tips by moving the microtiter plates slowly in a circular motion. Scrubbing was continued for 10 seconds. With the microtiter plate in contract with the harvester probe tips, scrubbing was continued and the "WASH" button was pressed for 10 seconds. Liquid was aspirated from wells and the above scrubbing steps were repeated. The plate was removed, the rinse tray filled with methanol, the tray raised, the methanol aspirated and the tray lowered.

The harvester was opened, with the filter mat adhering to the upper section and continued to operate on VAC for 5 seconds. After 5 seconds, the VAC was turned off and filter mat was removed from the harvester surface simultaneously. The filter mat was placed rough side up in drying oven for 10 minutes. The filter mats were removed from the oven and cooled to room temperature.

Counting of Radioactivity

All counting procedures were conducted in the Radioisotope Room. The filter mat loaded into counting cassette, rough side up. A collimator, thin stainless steal plate that holds filter mat in place, was placed over the filter mat. The cassettes were loaded into Packard Matrix 9600 Beta Particle Radioactivity Counter, and the flow of Q-Gas (1.3% n-butane in helium) started into Matrix 9600. The "START" button was pressed activating the counting protocol, counting the total radioactivity in each well for 3 minutes. Each sample count was stored in the hard drive of the Matrix 9600. In addition, a hard copy of the raw radioactivity counts was printed out.

Data Transformation

Data was downloaded from the Matrix 9600 hard drive onto a 3.5 diskette. The raw data was transformed into a reportable format using a macro executed in Microsoft Excel. This macro subtracts the plate background from each data point, generates an average for the triplicate well values, and presents this value as a percentage of the Plate Control value which is set equal to 100%.

Data Analysis (Normalization)

The antioxidant function of glutathione (GSH) was examined by lymphocyte growth response assay. The cells were placed in a chemically-defined, serum-free medium which contained 5 $\mu$M of L-Buthionine-(S,R)-sulfoximine (BSO), and the cells were stimulated to grow by the addition of a mitogenic compound. Growth response, measured by $^3$H-thymidine incorporation, is expressed as percentage of control growth. BSO suppresses the synthesis of glutathione transferase which is required for glutathione synthesis. Thus, the addition of BSO to the media and its suppression of glutathione synthesis is reflected by a change in cell growth, indicative of the status of glutathione in the lymphocyte. The doses of BSO used (5 $\mu$M) were established in 1995.

The individual's lymphocyte growth is expressed as a percentage of growth in media with or without BSO. Microsoft Excel was used to calculate the ratio of +BSO % growth to the 100% growth (without BSO). Over 1000 patient's result ratios are entered and statistical analysis was performed by standard Excel programs to determine mean, median, range and variance of the ratio. "Outliers", data that falls outside of a ±2 standard deviation range, were eliminated from the population base. The remaining data was used to determine the reference point and establish the population reference range. This population reference range was represented graphically as scatter plot distribution. The normal/reference value for glutathione has been determined to be greater than 85% (>85%); therefore, any person with a glutathione value of less than 85% will be classified as having a glutathione deficiency.

Equipment and Reagents

The following equipment was used in the assay of the present invention: Laminar Flow Hood; Centrifuge, Beckman GS-6; Cell Counter (Coulter Model T540); 12 Channel Pipettor (5–500 $\mu$l); Electric Pipet Pump (Drummond); Sterile 50 ml conical plastic tubes with caps; 12×75 mm polypropylene tubes; Sterile 15 ml conical plastic centrifuge tubes with caps; Pipettes (0–20, 0–200, 0–100 $\mu$l ranges); Sterile Glass Disposable Pipettes—5.0 ml, 10.0 ml; Test Tube Racks and Aerosol Barrier Pipet Tips (0–50 $\mu$l).

TABLE II shows the various reagents and their sources used in the method of the present invention:

TABLE II

| Reagents | | |
|---|---|---|
| Adenine Hydrochloride | Sigma | A 8751 |
| Antibiotic Solution (PSF) | GIBCO | 15245-012 |
| Arginine Hydrochloride | Sigma | A 5131 |
| L-Buthionine-[S.R]-Sulfoximine | Sigma | B2515 |
| d-Biotin | Sigma | B 4501 |
| Calcium Chloride, Anhydrous | Sigma | C 4901 |
| Choline Chloride | Sigma | C 1879 |
| Cumene Hydroperoxide | Sigma | C 0524 |
| Cyanocobalamin (Vit. $B_{12}$) | Sigma | V 2876 |
| Cystein Hydrochloride, Anhyd. | Sigma | C 1276 |
| Disodium EDTA | Sigma | E 4884 |
| Ferrous Sulfate Heptahydrate | Sigma | F 8633 |
| Folinic Acid, Calcium Salt | Sigma | F 7878 |
| Glucose | Sigma | G 5767 |
| Glucose Solution (10%) | Sigma | G 3126 |
| L-Glutamine | Sigma | G 3126 |
| Glycine | Sigma | G 7126 |
| HEPES, Free Acid | Sigma | H 3375 |
| L-Histidine(HCL monohydrate | Sigma | H 8125 |
| Histopaque (Ficoll/Diatrizoate) | Sigma | 1077-1 |
| Hydroxocobalamin(HCl ($B_{12}$) | Sigma | H 7126 |
| myo-Inositol | Sigma | I 5125 |
| L-Isoleucine | Sigma | I 2752 |
| L-Leucine | Sigma | L 8000 |
| L-Lysine | Sigma | L 5626 |
| Magnesium Sulfate, Anhydrous | Sigma | M 7506 |
| Methanol, Absolute | VWR | VWR4300-7 |
| L-Methionine | Sigma | M 9625 |
| Niacinamide (Vitamin $B_3$) | Sigma | N 3376 |
| D-Pantothenate, Calcium | Sigma | P 0290 |
| Phenol Red Solution, 0.5% PBS | Sigma | P 0290 |
| L-Phenylalanine | Sigma | P 2126 |
| PBS pH 7.4 | Sigma | P 3813 |
| Phytohemagglutinin PHA-P | Sigma | L 8754 |
| Potassium Phosphate, Dibasic | Sigma | P3786 |
| Pyridoxine(HCl (Vitamin $B_6$) | Sigma | P 9755 |
| Riboflavin (Vitamin $B_2$) | Sigma | R 4500 |
| L-Serine | Sigma | S 4500 |
| Sodium Chloride | Sigma | S 9625 |
| Sodium Hydroxide, 5.0N Solution | VWR | RS 415 1 |
| Sodium Pyruvate | Sigma | P 2256 |
| Sodium Pyruvate Sol. (100 mM) | Sigma | S 8636 |
| Thiamin (Vitamin $B_1$) | Sigma | T 4625 |
| L-Threonine | Sigma | T 8625 |
| Thymidine | Sigma | T 9250 |
| [$^3$H] - Thymidine | ICN | 24066 |
| L-Tryptophan | Sigma | T 0254 |
| L-Tyrosine | Sigma | T 3754 |
| L-Valine | Sigma | V 0500 |

Solutions

All solutions were prepared using tissue culture grade deionized water (tcd $H_2O$).

1. Phosphate Buffered Saline: To prepare a phosphate buffered saline (PBS)+0.72% Glucose (PBS-G) solution, PBS was prepared according to package instructions using tcd $H_2O$. Sufficient 10% glucose solution was added to achieve final glucose concentration of 0.72%. The solution was sterilized by filtration and stored in a refrigerator at (2–8° C.).

2. Stock Medium: A concentrated (2X) stock media was prepared in the following way: (1) 23.80 g HEPES; (2) 14.02 g Sodium Chloride; (3) 1.05 g Dibasic Potassium Phosphate; (4) 0.241 g Magnesium Sulfate; (5) 1.0 ml (10 $\mu$M) Adenine Hydrochloride; (6) 30.0 ml (100 mM) Sodium Pyruvate; (7) 0.5 ml 0.5% Phenol Red; (8) 5.0 ml Antibiotic Mixture; (9) 8.0 ml 5N Sodium Hydroxide; (10) 20.0 ml Fe/EDTA (1.0 mM $FeSO_4$/0.4 mM $Na_2EDTA$) were combined in tcd $H_2O$. After all materials had been mixed thoroughly, pH was adjusted to 7.60 using 5N Sodium Hydroxide. A final volume of 1.0 L was achieved with tcd $H_2O$. The solution was sterilized by filtration through a 0.2 $\mu$M filter and stored in a refrigerator at 4° C. Stability of the solution is 4 weeks.

3. Basal Medium: Basal Media used for 100% plate control and the novel method of the present invention is prepared as follows: After filtration, sterile technique should be employed. The Basal Media was prepared under laminar flow hoods, and the ingredients, as presented in Table III, were mixed and brought to the final desired volume with tcd $H_2O$. The solution was sterilized by vacuum filtration into sterile bottles. The proper volume of PHA Stock Solution was added.

4. L-Buthionine-[S.R.]-Sulfoximine (BS) Working Solution Preparation (5 $\mu$M/L): 0.2223 g BSO (Sigma B 2515) is dissolved in 20 ml PBS-G to make a 50 mM BSO stock solution. The solution is then sterilized by vacuum filtration into a sterile bottle using aseptic technique. A second BSO stock solution (500 $\mu$M) is prepared by adding 100 $\mu$l of 50 mM BSO into 900 $\mu$l sterile PBS-G. The 5 $\mu$M BSO working solution is prepared by adding 2.5 ml of the second, 500 $\mu$M BSO stock solution to 247.5 ml of Basal media and mixing well. The stability of this solution is for 1 week.

5. Thymidine(ThY) Stock Solution: The cold thymidine (ThY) stock solution (1.33 mM ThY, 0.322 g/L) was prepared as follows: 0.161 g ThY (Sigma T 9250) was weighed and dissolved in tcd $H_2O$ to final volume of 500 ml. The solution was sterilized by vacuum filtration into a sterile bottle using aseptic technique. The solution was aliquoted into 50 ml centrifuge tubes. For short-term storage, the solution can be refrigerated (4° C.) with stability for one month. For long-term storage, the solution can be frozen (−70° C.) with stability for 6 months. The thymidine working solution should be used to dilute radioactive thymidine ($H^3TdR$) for labeling of cells.

To prepare the thymidine working solution, ThY+$^3$H-TdR, the following chemicals were added to 300 ml sterile, de-gassed tcd $H_2O$: 1.15 ml of 1.33 mM ThY (Cold), 1.70 ml of $^3$H-TdR (ICN part #24066) with a specific activity of 300 $\mu$Ci/mmol. Once made, the solution may be stored under refrigerated conditions (4° C.) for 1 week.

EXAMPLE 4

Assessment of Cysteine Concentration Plate Inoculation

The final cell suspension was placed into a sterile trough and a microtiter plate containing media was placed inside a laminar flow hood. Using a 12-channel manual micropipettor equipped with sterile 0–50 $\mu$l barrier tips, the specified amount (according to TABLE IV) of final cell suspension was dispensed to each well of the plate.

TABLE IV

The following volumes are used for plate inoculation based on the listed final cell suspension Lymphocyte number (LY#).

| Final Cell Suspension LY# | Adjusted Volume For Inoculation |
|---|---|
| 3.9–.37 | 8.0 $\mu$l |
| 3.6 | 8.5 $\mu$l |
| 2.5–3.5 | 10.0 $\mu$l |
| 2.4 | 12.5 $\mu$l |

TABLE III

| STOCK SOLUTION | FINAL VOLUME BASAL MEDIA (ML) | | | | | |
|---|---|---|---|---|---|---|
| | 100 ml | 250 ml | 500 ml | 1000 ml | 1500 ml | 2000 ml |
| 2x Stock Media (ml) | 50 | 125 | 250 | 500 | 750 | 1000 |
| Thiamin ($B_1$) Stock ($\mu$l) | 10 | 25 | 50 | 100 | 150 | 200 |
| Riboflavin ($B_2$) Stock ($\mu$l) | 10 | 25 | 50 | 100 | 150 | 200 |
| Niacinamide ($B_3$) Stock ($\mu$l) | 10 | 25 | 50 | 100 | 150 | 200 |
| Pyridoxine (B6) Stock ($\mu$l) | 10 | 25 | 50 | 100 | 150 | 200 |
| Vitamin B12 Stock ($\mu$l) | 10 | 25 | 50 | 100 | 150 | 200 |
| 2nd Stock Folinic ($\mu$l) | 10 | 25 | 50 | 100 | 150 | 200 |
| Pantothenate Stock ($\mu$l) | 10 | 25 | 50 | 100 | 150 | 200 |
| Biotin Stock ($\mu$l) | 10 | 25 | 50 | 100 | 150 | 200 |
| Stock Glucose (ml) | 0.72 | 1.8 | 3.6 | 7.2 | 10.8 | 14.4 |
| Stock Chol/Ino (ml) | 1.0 | 2.5 | 5.0 | 10.0 | 15.0 | 20.0 |
| Stock All Aminos (ml) | 1.0 | 2.5 | 5.0 | 10.0 | 15.0 | 20.0 |
| Stock $CaCl_2$ (ml) | 0.5 | 1.25 | 2.5 | 5.0 | 7.5 | 10.0 |
| PHA (ml) | 0.2 | 0.5 | 1.0 | 2.0 | 3.0 | 4.0 |

TABLE IV-continued

The following volumes are used for plate inoculation based on the listed final cell suspension Lymphocyte number (LY#).

| Final Cell Suspension LY# | Adjusted Volume For Inoculation |
|---|---|
| 2.3 | 13.0 $\mu$l |
| 2.2 | 14.0 $\mu$l |
| 2.1 | 14.5 $\mu$l |
| 2.0 | 15.0 $\mu$l |
| 1.9 | 16.0 $\mu$l |
| 1.8 | 17.0 $\mu$l |
| 1.7 | 18.0 $\mu$l |
| 1.6 | 19.0 $\mu$l |
| 1.5 | 20.0 $\mu$l |

TABLE IV-continued

The following volumes are used for plate inoculation based on the listed final cell suspension Lymphocyte number (LY#).

| Final Cell Suspension LY# | Adjusted Volume For Inoculation |
|---|---|
| 1.4 | 21.5 µl |
| 1.3 | 23.0 µl |
| <=1.2 | 25.0 µl |

After addition of the cells to the media, 10 µl of N-Acetyl-L-Cysteine (150 mM as final concentration) solution was added to columns 1–9 In three rows of the plates.

In columns 1–3 of another six rows of the plate, 10 µl of 200 µM Cumene Hydroperoxide (CuOOH) was added. In columns 4–6 on six rows of the plate, 10 µl of 300 µM Cumene Hydroperoxide (CuOOH) was added. In columns 7–9 on six rows of the plate, 10 µl of 400 µM Cumene Hydroperoxide (CuOOH) was added. After addition of the CuOOH to the plates, the plates were covered and placed in a $CO_2$ incubator maintained at 37° for 96 hours.

Labeling

All labeling procedures were performed in the Radioisotope Room. The tritiated thymidine ($H^3$-TdR) working solution was removed from the refrigerator and warmed to 37° C. in a water bath. After 96 hours, the microtiter plates were removed from the incubator. The $H^3$-TdR working solution was placed in a sterile trough and a 12-channel manual micropipettor equipped with 0–50 µl sterile barrier tips was used to dispense 10 µl of the $H^3$-TdR working solution into each well of the microtiter plate. The plate was returned to the 37° C. incubator for 24 hours. The date and initials of the technician performing the labeling was recorded on the sample log sheet.

Harvesting

All harvesting procedures were performed in the Radioisotope Room. A single glass fiber filter mat (Packard Part # 6005416) was labeled with the sample number using a # 2 pencil. The vacuum pump was turned on and the drying oven set at 100° C. The distilled water carboy attached to the harvester was filled. The microtiter plates were removed from the incubator 24 hours after the addition of $H^3$-TdR. The date and initials of the technician performing harvesting was recorded on the sample log sheet.

With the Cell Harvester (Packard Model # C9619) in the open position, O-Rings exposed, the glass fiber filter mat was placed onto the harvester with the rough side touching the O-Rings. The cell harvester was closed and the filter mat was wet with distilled water from the rinse tray. The harvester was left on vacuum cycle (VAC). The lid was removed from microtiter plate and the plate was placed under harvester probe tips. The plate was slowly raised onto harvester probes, until the tips of the probe touched the bottom of the plate. With the media aspirated, the bottoms of the wells were scrubbed with the probe tips by moving the microtiter plates slowly in a circular motion. Scrubbing was continued for 10 seconds. With the microtiter plate in contract with the harvester probe tips, scrubbing was continued and the "WASH" button was pressed for 10 seconds. Liquid was aspirated from wells and the above scrubbing steps were repeated. The plate was removed, the rinse tray filled with methanol, the tray raised, the methanol aspirated and the tray lowered.

The harvester was opened, with the filter mat adhering to the upper section and continued to operate on VAC for 5 seconds. After 5 seconds, the VAC was turned off and filter mat was removed from the harvester surface simultaneously. The filter mat was placed rough side up in drying oven for 10 minutes. The filter mats were removed from the oven and cooled to room temperature.

Counting of Radioactivity

All counting procedures were conducted in the Radioisotope Room. The filter mat loaded into counting cassette, rough side up. A collimator, thin stainless steal plate that holds filter mat in place, was placed over the filter mat. The cassettes were loaded into Packard Matrix 9600 Beta Particle Radioactivity Counter, and the flow of Q-Gas (1.3% n-butane in helium) started into Matrix 9600. The "START" button was pressed activating the counting protocol, counting the total radioactivity in each well for 3 minutes. Each sample count was stored in the hard drive of the Matrix 9600. In addition, a hard copy of the raw radioactivity counts was printed.

Data Transformation

Data was downloaded from the Matrix 9600 hard drive onto a 3.5 diskette. The raw data was transformed into a reportable format using a macro executed in Microsoft Excel. This macro subtracts the plate background from each data point, generates an average for the triplicate well values, and presents this value as a percentage of the Plate Control value which is set equal to 100%.

Data Analysis (Normalization)

This test is an assessment of intracellular cysteine concentration, which is one determinant of a cell's antioxidant capacity. Using lymphocytes stimulated to grow by mitogen, the antioxidant function is expressed by comparing the difference in growth response of lymphocytes, with or without cysteine, in the presence of Cumene Hydroperoxide (CuOOH). The CuOOH creates the oxidative stress used to measure overall antioxidant status in individual patient. The addition of cysteine to the media provides an antioxidant with the ability to repair damage caused by the oxidative stress caused by CuOOH. The doses of CuOOH and cysteine were 300 µM and 150 µM, respectively.

The individual's lymphocyte growth expressed as a percentage of growth in media with CuOOH or cysteine+CuOOH. Microsoft Excel was used to calculate the ratio of Cysteine+CuOOH growth to the CuOOH % growth. More than 1000 patient's result ratios were entered for statistical analysis by standard Excel programs to determine the mean, median, range and variance. Outliers—data that falls outside of a ±2 standard deviation range—were eliminated from the population base. The remaining data was used to determine the reference point and establish the population reference range. This population reference range was graphically represented as scatter plot distribution. The normal/reference value for cysteine has been determined to be less than 127% (<127%), therefore, any person with a cysteine value of 127% or greater will be classified as having a cysteine deficiency.

Equipment and Reagents

The following equipment was used in the assay of the present invention: Laminar Flow Hood; Centrifuge, Beckman GS-6; Cell Counter (Coulter Model T540); 12 Channel Pipettor (5–500 µl); Electric Pipet Pump (Drummond); Sterile 50 ml conical plastic tubes with caps; 12×75 mm polypropylene tubes; Sterile 15 ml conical plastic centrifuge tubes with caps; Pipettes (0–20, 0–200, 0–100 µl ranges); Sterile Glass Disposable Pipettes—5.0 ml, 10.0 ml; Test Tube Racks and Aerosol Barrier Pipet Tips (0–50 µl).

TABLE V shows the various reagents and their sources used in the method of the present invention:

TABLE V

| Reagents | | |
|---|---|---|
| Adenine Hydrochloride | Sigma | A 8751 |
| Antibiotic Solution (PSF) | GIBCO | 15245-012 |
| Arginine Hydrochloride | Sigma | A 5131 |
| N-Acetyl-L-Cysteine | Sigma | A8199 |
| d-Biotin | Sigma | B 4501 |
| Calcium Chloride, Anhydrous | Sigma | C 4901 |
| Choline Chloride | Sigma | C 1879 |
| Cumene Hydroperoxide | Sigma | C 0524 |
| Cyanocobalamin (Vit. $B_{12}$) | Sigma | V 2876 |
| Cystein Hydrochloride, Anhyd. | Sigma | C 1276 |
| Disodium EDTA | Sigma | E 4884 |
| Ferrous Sulfate Heptahydrate | Sigma | F 8633 |
| Folinic Acid, Calcium Salt | Sigma | F 7878 |
| Glucose | Sigma | G 5767 |
| Glucose Solution (10%) | Sigma | G 3126 |
| L-Glutamine | Sigma | G 3126 |
| Glycine | Sigma | G 7126 |
| HEPES, Free Acid | Sigma | H 3375 |
| L-Histidine(HCL monohydrate | Sigma | H 8125 |
| Histopaque (Ficoll/Diatrizoate) | Sigma | 1077-1 |
| Hydroxocobalamin(HCI ($B_{12}$) | Sigma | H 7126 |
| myo-Inositol | Sigma | I 5125 |
| L-Isoleucine | Sigma | I 2752 |
| L-Leucine | Sigma | L 8000 |
| L-Lysine | Sigma | L 5626 |
| Magnesium Sulfate, Anhydrous | Sigma | M 7506 |
| Methanol, Absolute | VWR | VWR4300-7 |
| L-Methionine | Sigma | M 9625 |
| Niacinamide (Vitamin $B_3$) | Sigma | N 3376 |
| D-Pantothenate, Calcium | Sigma | P 0290 |
| Phenol Red Solution, 0.5% PBS | Sigma | P 0290 |
| L-Phenylalanine | Sigma | P 2126 |
| PBS pH 7.4 | Sigma | P 3813 |
| Phytohemagglutinin PHA-P | Sigma | L 8754 |
| Potassium Phosphate, Dibasic | Sigma | P3786 |
| Pyridoxine(HCI (Vitamin $B_6$) | Sigma | P 9755 |
| Riboflavin (Vitamin $B_2$) | Sigma | R 4500 |
| L-Serine | Sigma | S 4500 |
| Sodium Chloride | Sigma | S 9625 |
| Sodium Hydroxide, 5.0N Solution | VWR | RS 415 1 |
| Sodium Pyruvate | Sigma | P 2256 |
| Sodium Pyruvate Sol. (100 mM) | Sigma | S 8636 |
| Thiamin (Vitamin $B_1$) | Sigma | T 4625 |
| L-Threonine | Sigma | T 8625 |

TABLE V-continued

| Reagents | | |
|---|---|---|
| Thymidine | Sigma | T 9250 |
| [$^3$H] - Thymidine | ICN | 24066 |
| L-Tryptophan | Sigma | T 0254 |
| L-Tyrosine | Sigma | T 3754 |
| L-Valine | Sigma | V 0500 |

Solutions

All solutions were prepared using tissue culture grade deionized water (tcd $H_2O$).

1. Phosphate Buffered Saline: To prepare a phosphate buffered saline (PBS)+0.72% Glucose (PBS-G) solution, PBS was prepared according to package instructions using tcd $H_2O$. Sufficient 10% glucose solution was added to achieve final glucose concentration of 0.72%. The solution was sterilized by filtration and stored in a refrigerator at (2–8° C.).

2. Stock Medium: A concentrated (2X) stock media was prepared in the following way: (1) 23.80 g HEPES; (2) 14.02 g Sodium Chloride; (3) 1.05 g Dibasic Potassium Phosphate; (4) 0.241 g Magnesium Sulfate; (5) 1.0 ml (10 $\mu$M) Adenine Hydrochloride; (6) 30.0 ml (100 mM) Sodium Pyruvate; (7) 0.5 ml 0.5% Phenol Red; (8) 5.0 ml Antibiotic Mixture; (9) 8.0 ml 5N Sodium Hydroxide; (10) 20.0 ml Fe/EDTA (1.0 mM $FeSO_4$/0.4 mM $Na_2EDTA$) were combined in tcd $H_2O$. After all materials had been mixed thoroughly, pH was adjusted to 7.60 using 5N Sodium Hydroxide. A final volume of 1.0 L was achieved with tcd $H_2O$. The solution was sterilized by filtration through a 0.2 $\mu$M filter and stored in a refrigerator at 4° C. Stability of the solution is about 4 weeks.

3. Basal Medium: Basal Media used for 100% plate control and the novel method of the present invention is prepared as follows: After filtration, sterile technique should be employed. The Basal Media was prepared under laminar flow hoods, and the ingredients, as presented in Table VI, were mixed and brought to the final desired volume with tcd $H_2O$. The solution was sterilized by vacuum filtration into sterile bottles. The proper volume of PHA Stock Solution was added.

TABLE VI

| STOCK SOLUTION | FINAL VOLUME BASAL MEDIA (ML) | | | | | |
|---|---|---|---|---|---|---|
| | 100 ml | 250 ml | 500 ml | 1000 ml | 1500 ml | 2000 ml |
| 2x Stock Media (ml) | 50 | 125 | 250 | 500 | 750 | 1000 |
| Thiamin ($B_1$) Stock ($\mu$l) | 10 | 25 | 50 | 100 | 150 | 200 |
| Riboflavin ($B_2$) Stock ($\mu$l) | 10 | 25 | 50 | 100 | 150 | 200 |
| Niacinamide ($B_3$) Stock ($\mu$l) | 10 | 25 | 50 | 100 | 150 | 200 |
| Pyridoxine ($B_6$) Stock ($\mu$l) | 10 | 25 | 50 | 100 | 150 | 200 |
| Vitamin B12 Stock ($\mu$l) | 10 | 25 | 50 | 100 | 150 | 200 |
| 2nd Stock Folinic ($\mu$l) | 10 | 25 | 50 | 100 | 150 | 200 |
| Pantothenate Stock ($\mu$l) | 10 | 25 | 50 | 100 | 150 | 200 |
| Biotin Stock ($\mu$l) | 10 | 25 | 50 | 100 | 150 | 200 |
| Stock Glucose (ml) | 0.72 | 1.8 | 3.6 | 7.2 | 10.8 | 14.4 |
| Stock Chol/Ino (ml) | 1.0 | 2.5 | 5.0 | 10.0 | 15.0 | 20.0 |
| Stock All Aminos (ml) | 1.0 | 2.5 | 5.0 | 10.0 | 15.0 | 20.0 |
| Stock $CaCl_2$ (ml) | 0.5 | 1.25 | 2.5 | 5.0 | 7.5 | 10.0 |
| PHA (ml) | 0.2 | 0.5 | 1.0 | 2.0 | 3.0 | 4.0 |

4. Cumene Hydroperoxide (CuOOH) Stock Solutions; Cumene hydroperoxide (Sigma C 0524) has a limited shelf life. Expiration date of the material is three (3) months from date of receipt from Sigma. When pipetting CuOOH from the bottle, one should be aware of the increased viscosity of CuOOH. One must ensure that aspiration of liquid into the pipet tip is complete. This requires extra time and attention to ensure adequate fill of pipet tip. Also, one must wipe the tip to remove excess CuOOH on the outside of the pipet tip. Likewise, one must dispense the CuOOH completely. Following this procedure, one may store the solution under refrigerated conditions (2–8° C.) with stability for up to 3 months.

For the first CuOOH stock solution (1.0 M CuOOH in PBS-G), 9.5 µl cumene hydroperoxide (CuOOH) are mixed with 990.5 µl PBS-G. Following this procedure, one may store the solution under refrigerated conditions (2–8° C.) with stability for up to 3 months.

The second CuOOH stock solution (100 mM in PBS-G) must be prepared daily before cell isolation, and should not be stored overnight. To prepare the second CuOOH stock solution, 200 µl of the first stock solution were mixed with 1800 µl of PBS-G.

For the cumene hydroperoxide working solutions, 4 working solutions were prepared daily before cell isolation. The solution was added to the CuOOH Transfer Plate (separate microtiter plate) for loading of patient plates. The solutions should not be stored overnight. The working solution was 300 µM CuOOH: 330 µl of the second CuOOH stock solution was mixed with 4670 µl PBS-G.

5. Thymidine(ThY) Stock Solution: The cold thymidine (ThY) stock solution (1.33 mM ThY, 0.322 g/L) was prepared as follows: 0.161 g ThY (Sigma T 9250) was weighed and dissolved in tcd $H_2O$ to final volume of 500 ml. The solution was sterilized by vacuum filtration into a sterile bottle using aseptic technique. The solution was aliquoted into 50 ml centrifuge tubes. For short-term storage, the solution can be refrigerated (4° C.) with stability for one month. For long-term storage, the solution can be frozen (−70° C.) with stability for 6 months. The thymidine working solution should be used to dilute radioactive thymidine ($H^3TdR$) for labeling of cells.

To prepare the thymidine working solution, ThY+$^3$H-TdR, the following chemicals were added to 300 ml sterile, de-gassed tcd $H_2O$: 1.15 ml of 1.33 mM ThY (Cold), 1.70 ml of $^3$H-TdR (ICN part #24066), and 300 µCi/mmol specific activity. Once made, the solution may be stored under refrigerated conditions (4° C.) for 1 week.

6. N-Acetyl-L-Cysteine (NAC) Working Solution: 0.0702 g of N-Acetyl-L-Cysteine (Sigma A8199) was dissolved in 4 ml PBS-G solution to form a final concentration 0.1M stock solution. This stock solution was dispensed in 1 ml aliquots into 12×75 sterile tubes, and these aliquots may be stored up to one week in the freezer at −70° C. To make the working solution, take 990 µl of one aliquot of the 0.1M NAC stock solution and add to 29.01 ml of the PBS-G solution and mix well. The working solution should be sterilzed by vacuum filtration into a sterile bottle, using aseptic technique. Finally, 10 µl of this solution should be added into the triplicate test wells. It is important that the N-Acetyl-L-Cysteine working solution should be made fresh every day before the test is performed.

One skilled in the art will appreciate readily that the present invention is well adapted to carry out the objects and obtain the ends and advantages mentioned, as well as those objects, ends and advantages inherent herein. The present examples, along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. An N-acetyl-L-cysteine cell culture medium (NAC medium) comprising;
   a buffered, serum-free solution having a pH value from about 6.8 to about 7.6, said solution containing:
   glucose;
   a biologically utilizable form of pantothenic acid or choline;
   at least one inorganic ion in a biologically utilizable form, wherein said ion is chloride ion, phosphate ion, calcium ion, magnesium ion, potassium ion, sodium ion, or iron ion;
   cumene hydroperoxide, wherein said cumene hydroperoxide is present in a concentration of about 5 µM to about 500 µM;
   deionized water,
   N-acetyl-L-cysteine (NAC);
   a mitogen wherein said mitogen stimulates said lymphocytes to grow; and
   optionally, at least one of a supplemental nutrient in a biological utilizable form wherein said supplemental nutrient is:
   a) an L-amino acid;
   b) a vitamin; or
   c) at least one of pyruvate, adenine or inositol.

2. The cell culture medium of claim 1, wherein said L-amino acid is selected from the group consisting of L-arginine, L-cysteine, L-glutamine, glycine, L-histidine, L-isoleucine, L-leucine, L-lysine, L-methionine, L-phenylalanine, L-serine, L-threonine, L-tryptophan, L-tyrosine, and L-valine.

3. The cell culture medium of claim 1, wherein said vitamin is selected from the group consisting of biotin, folinic acid, nicotinamide, nicotinic acid, riboflavin, thiamin, vitamin $B_6$, and vitamin $B_{12}$.

4. The cell culture medium of claim 1, wherein at least one of said pyruvate, said adenine or said inositol supplements said cell culture medium at concentrations eliciting approximately a maximal growth response.

5. An N-acetyl-L-cysteine cell culture medium (NAC medium) comprising:
   a serum-free cell culture medium;
   cumene hydroperoxide; and
   N-acetyl-L-cysteine (NAC).

6. The N-acetyl-L-cysteine cell culture medium of claim 5, wherein said cumene hydroperoxide is present in a concentration of about 5 µM to about 500 µM.

7. The N-acetyl-L-cysteine cell culture medium of claim 5, further comprising glucose.

8. The N-acetyl-L-cysteine cell culture medium of claim 7, further comprising a biologically utilizable form of pantothenic acid or choline.

9. The N-acetyl-L-cysteine cell culture medium of claim 8, further comprising at least one inorganic ion in a biologically utilizable form, wherein said ion is chloride ion, phosphate ion, calcium ion, magnesium ion, potassium ion, sodium ion, or iron ion.

10. The N-acetyl-L-cysteine cell culture medium of claim 9, further comprising deionized water.

11. The N-acetyl-L-cysteine cell culture medium of claim 10, further comprising a mitogen wherein said mitogen stimulates lymphocytes to grow.

12. The N-acetyl-L-cysteine cell culture medium of claim 11, further comprising at least one of a supplemental nutrient in a biological utilizable form wherein said supplemental nutrient is:

a) an L-amino acid;

b) a vitamin; or c) at least one of pyruvate, adenine or inositol.

13. The N-acetyl-L-Cysteine cell culture medium of claim 12, wherein said cumene hydroperoxide is present in a concentration of about 5 $\mu$M to about 500 $\mu$M.

14. The N-acetyl-L-cysteine cell culture medium of claim 12, wherein said L-amino acid is selected from the group consisting of L-arginine, L-cysteine, L-glutamine, glycine, L-histidine, L-isoleucine, L-leucine, L-lysine, L-methionine, L-phenylalanine, L-serine, L-threonine, L-tryptophan, L-tyrosine, and L-valine.

15. The N-acetyl-L-cysteine cell culture medium of claim 12, wherein said vitamin is selected from the group consisting of biotin, folinic acid, nicotinamide, nicotinic acid, riboflavin, thiamin, vitamin $B_6$, and vitamin $B_{12}$.

16. The N-acetyl-L-cysteine cell culture medium of claim 12, wherein at least one of said pyruvate, said adenine or said inositol supplements said cell culture medium at concentrations eliciting approximately a maximal growth response.

* * * * *